US010981686B2

(12) United States Patent
Dey et al.

(10) Patent No.: US 10,981,686 B2
(45) Date of Patent: Apr. 20, 2021

(54) UNIVERSAL WINDING MACHINE FOR A MULTITUDE OF TRAY DESIGNS

(71) Applicant: Harro Hoefliger Verpackungsmaschinen GmbH, Allmersbach im Tal (DE)

(72) Inventors: Clifford Dey, Allmersbach im Tal (DE); Juergen Gattnar, Allmersbach im Tal (DE); Bernhard Waechter, Allmersbach im Tal (DE)

(73) Assignee: Harro Hoefliger Verpackungsmaschinen GmbH, Allmersbach im Tal (DE)

( * ) Notice: Subject to any disclaimer, the term of this patent is extended or adjusted under 35 U.S.C. 154(b) by 152 days.

(21) Appl. No.: 16/047,454

(22) Filed: Jul. 27, 2018

(65) Prior Publication Data
US 2019/0039769 A1 Feb. 7, 2019

(30) Foreign Application Priority Data
Aug. 1, 2017 (EP) .................................... 17001348

(51) Int. Cl.
*B65B 63/04* (2006.01)
*A61B 17/06* (2006.01)
(Continued)

(52) U.S. Cl.
CPC ........ *B65B 63/04* (2013.01); *A61B 17/06114* (2013.01); *A61B 17/06133* (2013.01);
(Continued)

(58) Field of Classification Search
CPC ............... B65B 63/04; A61B 17/06114; A61B 17/06133; A61B 2017/00526;
(Continued)

(56) References Cited

U.S. PATENT DOCUMENTS 5,052,551 A 10/1991 Cerwin et al.
5,271,495 A * 12/1993 Alpern ............. A61B 17/06133
206/380

(Continued)

FOREIGN PATENT DOCUMENTS

CN 1112823 A 12/1995
CN 104647652 A 5/2015
(Continued)

OTHER PUBLICATIONS

European Search Report in EP 17001348.6 dated Feb. 2, 2018.
(Continued)

*Primary Examiner* — Nathaniel C Chukwurah
*Assistant Examiner* — Lucas E. A. Palmer
(74) *Attorney, Agent, or Firm* — Collard & Roe, P.C.

(57) ABSTRACT

A machine for winding suture into a suture tray package includes a base platform with package nests, each nest including upwardly-extending locating pins. A workstation places an empty tray onto one nest. Another workstation feeds a needle with attached suture in the tray and parks the needle in the tray. A winding station for winding the suture into a tray winding channel includes a rotatable winding head with configurable suture guiding pins, a stripper plate pushing the wound suture off the guiding pins, a suture control arm with proximal and distal ends and top and bottom sides, the distal end having a front standoff and a rear standoff incorporating a suture guiding channel, and a base member mounting the arm to base platform. A lid placement station places a lid onto a nest, a lid attachment station attaches lid to tray and an offloading station removes trays from nests.

2 Claims, 5 Drawing Sheets

(51) Int. Cl.
*B65H 54/04* (2006.01)
*B65H 54/22* (2006.01)
*B65H 54/58* (2006.01)
*A61B 17/00* (2006.01)

(52) U.S. Cl.
CPC ............. *B65H 54/04* (2013.01); *B65H 54/22* (2013.01); *B65H 54/58* (2013.01); *A61B 2017/00526* (2013.01); *A61B 2017/06142* (2013.01); *B65H 2701/3918* (2013.01)

(58) Field of Classification Search
CPC .......... A61B 2017/06142; B65H 54/58; B65H 54/22; B65H 54/04
See application file for complete search history.

(56) References Cited

U.S. PATENT DOCUMENTS

| | | | |
|---|---|---|---|
| 5,487,216 A | | 1/1996 | Demarest et al. |
| 5,660,024 A | * | 8/1997 | Ivanov ................... B65B 63/04 53/116 |
| 5,661,954 A | * | 9/1997 | Ivanov ................... B65B 35/26 53/116 |
| 5,664,404 A | * | 9/1997 | Ivanov ................... B65B 19/34 53/430 |
| 5,695,138 A | * | 12/1997 | Daniele ............ A61B 17/06133 242/159 |
| 6,047,815 A | | 4/2000 | Cerwin et al. |
| 6,135,272 A | | 10/2000 | Sobel et al. |
| 6,463,719 B2 | * | 10/2002 | Dey ................. A61B 17/06133 206/63.3 |
| 6,644,469 B2 | * | 11/2003 | Alpern ............ A61B 17/06133 206/380 |
| 6,804,937 B2 | | 10/2004 | Dey et al. |
| 8,011,499 B2 | * | 9/2011 | McHugh Karow ........................ A61B 17/06119 206/63.3 |
| 2004/0177594 A1 | * | 9/2004 | Dey ................. A61B 17/06133 53/430 |
| 2008/0017526 A1 | * | 1/2008 | Prescott ........... A61B 17/06133 206/63.3 |
| 2008/0185752 A1 | | 8/2008 | Cerwin et al. |
| 2016/0317148 A1 | | 11/2016 | Martinez |

FOREIGN PATENT DOCUMENTS

| | | |
|---|---|---|
| EP | 0 760 228 A1 | 3/1997 |
| JP | S60-209470 A | 10/1985 |
| WO | 2016/175935 A1 | 11/2016 |

OTHER PUBLICATIONS

Indian Office Action in in 201814028946 dated Apr. 21, 2020.
Chinese Office Action in Chinese Application No. 201810859501.3, dated Sep. 2, 2020 with English translation.

* cited by examiner

UNIVERSAL WINDING MACHINE FOR A MULTITUDE OF TRAY DESIGNS

CROSS REFERENCE TO RELATED APPLICATIONS

Applicant claims priority under 35 U.S.C. § 119 of European Application No. 17001348.6 filed Aug. 1, 2017, the disclosure of which is incorporated by reference.

BACKGROUND OF THE INVENTION

1. Field of the Invention

This invention relates to packages for surgical sutures and surgical needles, more particularly to equipment for winding surgical sutures and attached surgical needles into suture packages. Conventional surgical suture and needle packages serve several useful functions, including protecting the needles and sutures during handling, shipping, and storage. In addition, the packages facilitate access and release of the needles and sutures during surgery or other medical procedures prior to application. The packages may be used for surgical sutures armed with surgical needles or for unarmed surgical sutures without needles.

2. Description of the Related Art

Surgical needles and attached surgical sutures are well known in the art. Surgical needles and sutures are packaged in a variety of packages for delivery of the needles and sutures to the surgeon. The packages need to have a number of important characteristics, including ease of loading, ease of dispensing, and protection of the needle and the suture during handling, sterilization, shipping and storage.

The common tray-type packages having a peripheral channel formed by a bottom channel with attached top portion with flaps or doors for receiving a suture are commonly used to package needles and suture combinations. These tray packages are typically made with moveable doors or members that cover the top of the track to prevent the suture from moving out of the track. These tray packages have a number of advantages. For example, the packages are relatively inexpensive to manufacture and are typically molded from biocompatible, inert polymeric materials. The track packages provide excellent protection to the sutures during processing, sterilization, shipment and storage. The packages are easy to handle by the surgical staff, and sutures are easy to withdraw from the tray packages in a consistent manner without tangles or lock-ups. One particular advantage of tray packages is their ease of suture loading in high speed, automated packaging process. Examples of tray packages are disclosed in U.S. Pat. Nos. 6,135,272, 6,047,815, 6,644,469, and 8,011,499.

Surgical sutures are packaged in tray packages by using conventional winding fixtures. The fixture typically has a rotatable base with mounting pins. A tray package is mounted on the base and the pins such that the top of the tray package is facing upwardly. Then a winding stylus mounted to a winding head directs a length of suture down into a track of the suture tray. As the tray rotates the stylus rides or touches the bottom thereby opening the upper or lid flaps so that the suture is placed in the track in a uniform manner. Examples of such winding fixtures and styluses are disclosed in U.S. Pat. Nos. 5,660,024, 5,664,404, 6,804,937 and 6,463,719.

Although conventional winding processes with winding fixtures and styluses perform adequately for their intended use, there may be deficiencies associated with such winding processes.

For example, the current winding processes require a plastic tray with both a top piece and a bottom piece attached together. The top piece needs to have flaps or doors for receiving a suture. These flaps need to be opened to allow the suture to be guided in. This does not allow for other designs of packages such as a plastic tray consisting of a single piece bottom only or a side loaded package. The opening of the flaps influences the rpm (rounds per minute) that the package can be run at due to damage caused as the stylus impacts and pushes the flaps up.

Also for example, a stylus in a conventional winding fixture is rigidly mounted to the winding fixture and this does not allow for variations in the dimensions of tray packages. This may also result in potentially improper placement of the suture in the track of the package. This is caused because the stylus uses its back heel and its top along with the floor of the package to form the guidance of the suture. The suture changes speed as it is wound in an oval tray. It moves fast on the straight part of the tray while slowing down as it is going around the corners. Therefore, the suture can be anywhere from being on the floor of the tray during deceleration to being in contact with the top of the stylus during acceleration.

Also the automated winding processes where the needle is automatically placed in the suture tray and then automatically wound are limited to single arm sutures of about 5/0 and above. The double armed sutures are typically hand placed in a plastic tray or a paper tray. The sutures in the smaller sizes are typically also hand placed in a foam retainer on a paper tray. There are new suture retainers that are being developed to reduce medical waste by going to a plastic bottom with a channel and a paper lid that also serves as a label. The paper is required as a desiccant for the suture but there is not a current process to wind automatically.

There is a need in this art for a novel automated suture tray winding process that overcomes the deficiencies of the prior art and that will be easily and quickly adapted for all of the new and the old suture trays both top load or side load. Also there is a need to automatically load and wind micro needles and micro sutures and double armed sutures.

SUMMARY OF THE INVENTION

Proceeding from this previously known prior art, it is an object of the present invention to provide a novel suture winding machine which can be easily adapted for different designs of tray packages and which is useful in a high-speed packaging process for packaging surgical sutures.

Accordingly, a novel adaptive suture and tray process is disclosed. This process starts with a multi station machine. It can be circular or inline and can contain as many stations as desired. The preferred embodiment is an eight station rotary type machine. The idea is to maintain the basic design while allowing for different tray designs such as
 one piece bottom with paper top,
 one piece bottom with flat plastic top
 two piece bottom with a top with pedals or doors and
  paper lid,
 a tray without an outside lip or
 a tray with sideloading of suture.
The machine has a top plate with modular mounting holes for off the shelf stations as required by the intended use. For example, there could be a manual needle load and a manual package unload. There could also be a fully automated needle load and unload.

The first station would be for the infeed of the desired tray using existing methods and devices.

The second station is fundamentally open for custom modules required for packages such as pre-arming a needle retention area or adding a piece of foam for small needles. This station could also provide confirmation of tray present.

The third station is for the loading of the needle. Additionally attached to station three can be a loading slide. This slide allows for the manual placing of the needle to be transported to the transfer to the tray. This is designed to accommodate double armed sutures down to 5/0. With a quick change of the slide grippers and robot grippers it will accommodate needle to 8/0 sutures (8 millimeter needles). The transfer of micro-needles with attached sutures into foam having been attached in a prior station can be robotically performed. This loading slide will also have locating points to attach an automated crimping station with direct loading of single armed suture sets.

Station four of the present invention is a suture winding assembly. The suture winding assembly has a nest member for receiving a suture tray package having a winding channel. The assembly can provide a vacuum for assisting the winding of the sutures into a one-piece bottom tray. The assembly also has a winding head for rotatability and engaging the nest and tray package. Furthermore, the winding assembly has a suture control arm with a base member. The base member can have a top side, a bottom side and opposed front and rear lateral sides. The suture control arm can have a top side and a bottom side with a frontal opening mechanism fundamentally in a rounded shape. Furthermore, there is a U-shaped member at the rear of the suture control arm that controls the entry point and the height of the suture. This facilitates the alignment of the suture wind therefore allowing for an easier removal of the suture. The suture control arm does not need to ride on the bottom of the tray floor in order to capture the suture. Therefore, the same suture control arm can be used, independent of the height of the wall of the tray and independent of the kind of tray (top-loading or side-loading).

The suture control arm is mounted to the base member. An outer ring that maintains the relative relationship of the suture control arm to the inside of the suture track of the package is formed to the rotatable winding head. The base member with the mounted suture control arm can be engaged in this outer ring. This could be realized by one or more running pulleys at the base member.

The assembly also has a novel suture winding head with a multitude of suture guiding pins that either touch the floor of the tray or extend through it. These suture guiding pins have an angle to facilitate the control of the winds. There is a stripper plate that pushes down after winding and before the winding head disengages the winding nest. This stripping motion causes the sutures to lay in a controlled manner.

Station five is for the lid placement. Either a paper lid or a plastic top can be placed by this station. When the winding of the suture is performed under vacuum, station four is usually followed by station five. Nevertheless, if the winding of the suture is done without vacuum, it can be advantageous to have station five followed by station four.

Station six is for the lid attachment. For example, there could be either staking or ultrasonic attachment.

Station seven is the offload station to an intermediate station. In this station, a camera inspection can be completed. There can be an offload to either an outfeed belt, a magazine, or a rejection bin.

Station eight will be used for the verification of a successful unloading operation.

Yet another aspect of the present invention is a method of winding a suture into a suture channel of a suture tray package using the suture control arm and the suture winding assembly specified above. This method can allow for speeds above 1000 rpm (rounds per minute). The state of the art is usually less than 400 rpm.

The vacuum can be supplied in a constant manner from station four to station six as required by the package design.

These and other features and advantages of the present invention will become more apparent from the following description and accompanying drawings.

Further advantages and features of the invention can be gathered from the features which are further specified in the claims and from the following exemplary embodiments.

BRIEF DESCRIPTION OF THE DRAWINGS

In the following text, the invention will be described and explained in greater detail using the exemplary embodiments which are shown in the drawings.

DETAILED DESCRIPTION OF THE PREFERRED EMBODIMENTS

Figure 1:
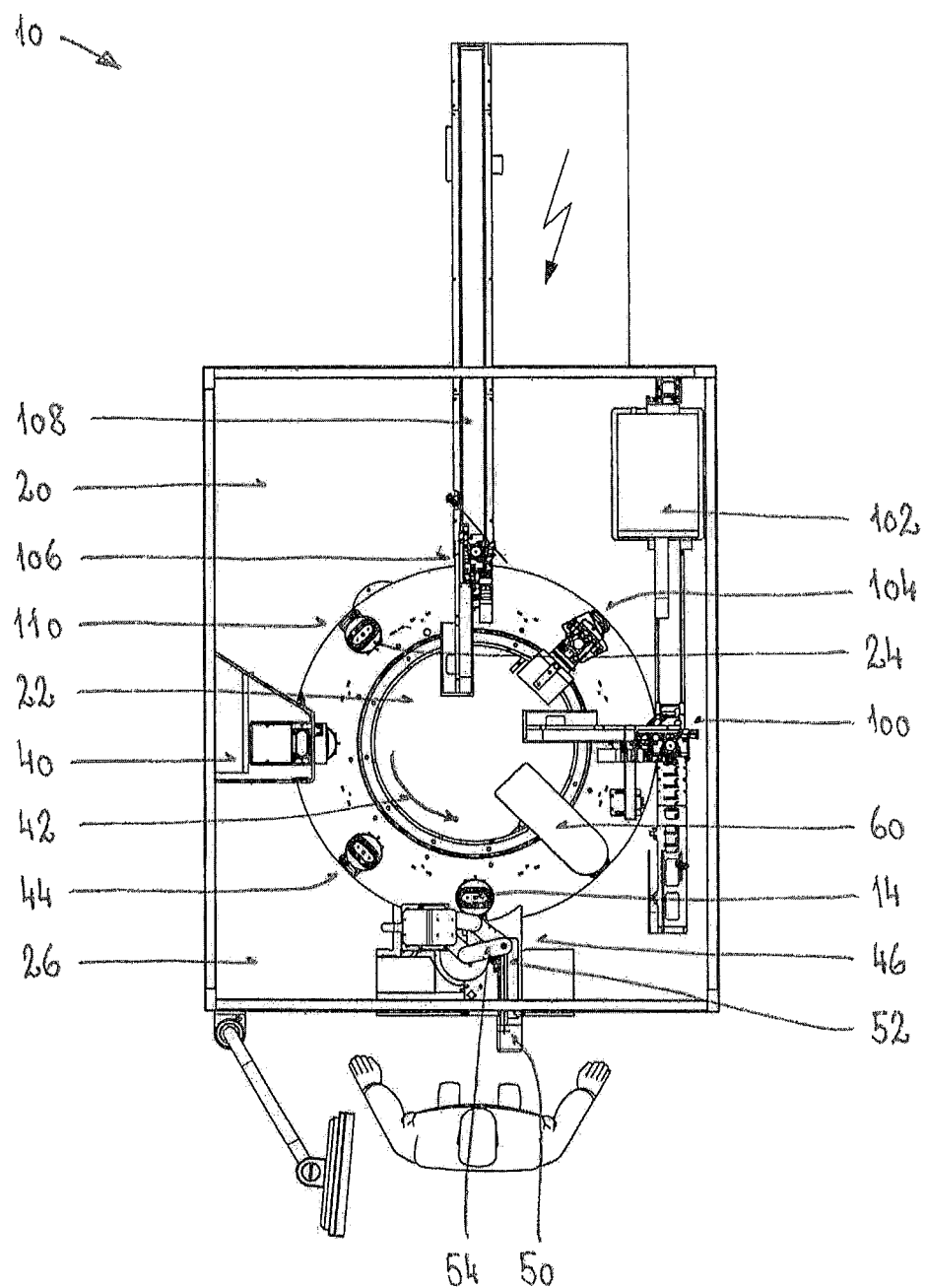
FIG. 1 is a schematic view of a first embodiment of the machine showing a manual winder.
Figure 2:
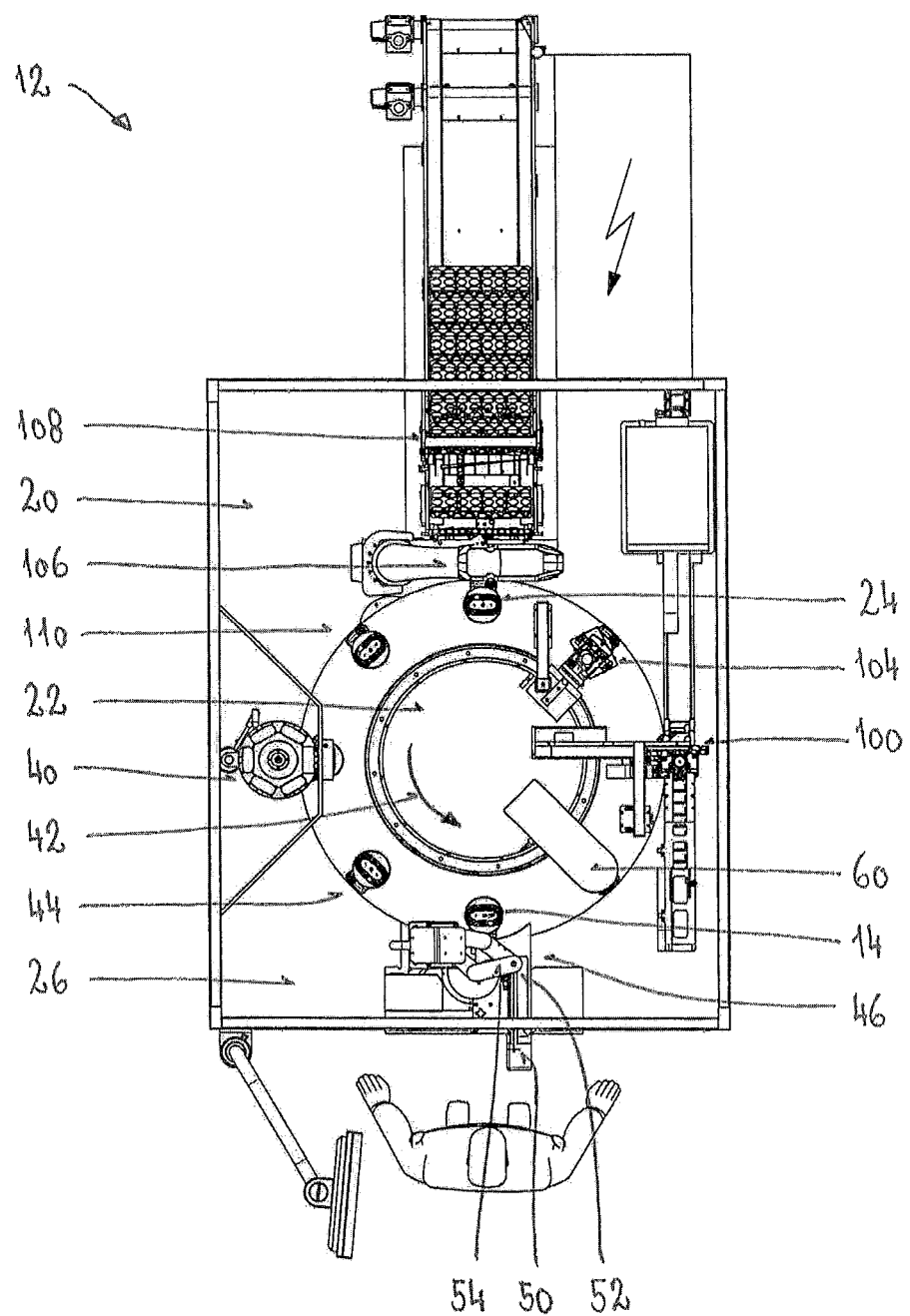
FIG. 2 is a schematic view of a second embodiment of the machine showing a semi-automatic winder.

The winding process of the present invention can be used in a manual suture winding machine 10 according to FIG. 1 or in a semi-automatic suture winding machine 12 according to FIG. 2. In both cases, tray suture packages 14 of various designs can be used. The shape of the tray 14 can be essentially circular to oval. It can also be oval with finger indentations on the outer periphery (peanut shape).

Referring to FIG. 1, the manual suture winding machine 10 has a base platform 20 with a rotary dial 22 mounted thereon. In this preferred embodiment there are eight package nests 24 on the rotary dial 22. Each of the package nests 24 is labelled so it will be possible to track the trays 14 during the winding process. There could be more than eight package nests 24 or less than this, depending on the number of stations necessary for the winding process.

This type of rotary dial 22 is widely used in the art so it is not described in detail. On the outside of the rotary dial 22 is the base plate 26 for mounting each of the stations. This modular design allows for quick customization of the stations as may be required by the design of the tray 14 or by station requirements.

Figure 3:
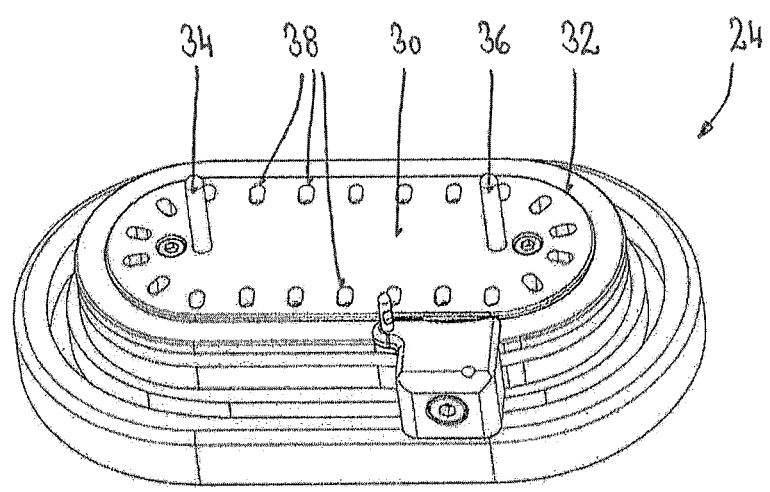
FIG. 3 is a schematic view of one of the winding nests of the machine according to FIG. 1 or 2 with a tray placed into it.

The package nest 24 is shown in greater detail in FIG. 3. The package nest 24 has an inset 30 with an oval cavity 32.

The cavity 32 is adapted for the specific tray 14 which is loaded into this cavity 32. In order to load a different tray 14, only the inset 30 has to be changed in order to accommodate a tray 14 with a different shape or a different diameter. The package nest 24 has two locating pins 34 and 36. The locating pins 34 and 36 reach through holes in the base member of the tray 14. The locating pins 34 and 36 can be mounted directly on the package nest 24 so they will be fixed in a specific position. In contrast to that, the locating pins 34 and 36 can be mounted on the inset 30 so they can be adapted according to the specific design of the tray 14. The package nest 24 is capable of creating a vacuum through slots (not shown) that match the air slots 38 of the tray 14. Those slots can also be adapted according to the specific design of the tray 14. Therefore, only the inset 30 of the package nest 24 has to be changed in order to adapt the winding machine 10 for different designs of trays 14. There is no need for a further adjustment performed by an operator.

The first station 40 is the tray infeed. This station 40 is shown at nine o'clock of the rotary dial 22 according to FIG. 1. This type of infeed station 40 is widely used in the art so it is not described in detail. In principal, there are two options. There could be a single stack of trays 14 to be loaded into the package nests 24 or there could be a multi stack carrousel. In both cases the trays 14 are singularized and placed onto the package nests 24.

In the shown embodiment, the package nests 24 are rotated in an anticlockwise direction 42. The second station 44 is an open station for further options. For example, this station 44 could be used to load a top of the tray 14. It would also be possible to cut and place a foam in this station 44. If micro-needles do not fit into the needle park of the tray, such a foam might be necessary.

In the third station 46 a needle with an attached suture is fed in and parked in the tray 14. The needles are fed by an operator onto the loading shuttle 50. The loading shuttle 50 then moves in a linear motion to the pickup station 52. A motion slide like this is widely used in the art so it is not described in detail. At the pickup station 52 the robot grippers 54 grip the needles from the loading shuttle 50. The shuttle 50 then returns to its loading position. The robot grippers 54 now travel to the package nest 24 of the rotary dial 22 and load the needle into the needle park of the tray 14.

Depending on the kind and the size of the needle to be loaded into the needle park, it might be necessary to change the tools of the loading shuttle 50 and of the robot grippers 54. For micro-needles, the loading shuttle 50 should provide a novel land area for gripping these micro-needles. Furthermore, the robot grippers 54 should be changed to tweezer-type grippers. At the package nest 24, the micro-needles are rotated into the added foam park of the tray 14 and then released.

The fourth station 60 is the novel winding station. This station 60 is shown in greater detail in FIGS. 4 and 5. The winding station 60 has a novel winding head 62. This winding head 62 provides the winding machine 10 with several different options that will enable the winding machine 10 to work with trays 14 of different designs and shapes. The winding head 62 has configurable suture guiding pins 64. The suture guiding pins 64 engage the floor of the tray 14 and keep it flat. Furthermore, the suture guiding pins 64 in conjunction with the suture control arm 66 and in conjunction with the winding speed work to place the suture in a specific pattern into the winding channel of the tray 14. In order to facilitate the withdrawing of the suture, the first wind of the suture should be placed at the bottom of the winding pin and the last wind of the suture should be placed at the top. After finishing the winding a stripper plate 68 is actuated and pushes the suture off the suture guiding pins 64. The suture comes to lie on the bottom of the tray 14 in a controlled pattern.

The suture guiding pins 64 have an angle 70 on their end that is configurable. This angle depends on the needs of the package 14 and its requirements for size and shape.

The stripper plate 68 is able to hold a vacuum. This is necessary if the lid of the tray 14 can be placed before the winding of the suture. In this case, the stripper plate 68 will push the lid into its place at the same time it pushes the suture off the suture guiding pins 64. If the lid is placed after finishing the winding of the suture, the vacuum for the stripper plate 68 can be deactivated; it is also possible to do without the possibility of holding vacuum for the stripper plate 68.

Figure 6:
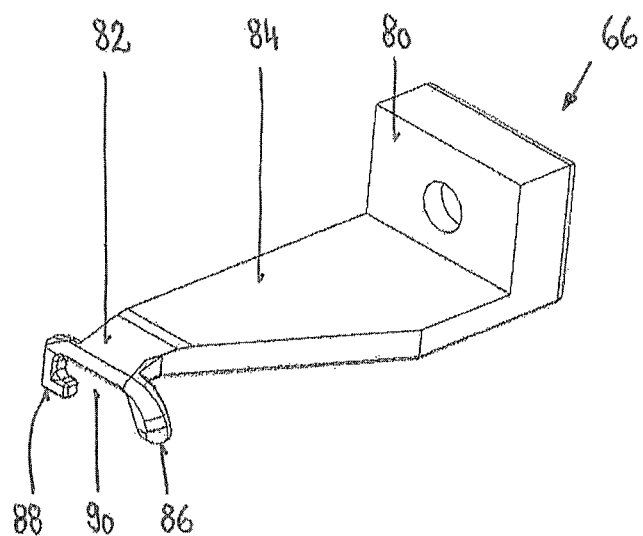
FIG. 6 is a schematic view of the suture control arm of the winding station according to FIG. 4.

The suture control arm 66 is shown in more detail in FIG. 6. The suture control arm 66 has a proximal end 80, a distal end 82, a top side 84, and a bottom side. The distal end 82 has a unique design that allows it to function with trays 14 that are top-loaded and trays that are side-loaded. This design also allows the suture control arm 66 to work with trays that have a top with pedals, a solid plastic top, a paper top, or no top at all. The distal end 82 of the suture control arm 66 has a front standoff 86 and a rear standoff 88 incorporating a suture guiding channel 90. The suture guiding channel 90 keeps the suture located in reference to the bottom of the tray 14 without back pressure because this may cause damage of the suture. The top of the front standoff 86 of the distal end 82 has a predominantly rounded shape. This shape lessens the impact of a plastic tray to or of pedals compared to an angled front and a flat top with a vertical drop at the back. The rear standoff 88 of the distal end 82 is basically a U-shaped member with the opening of the U pointing towards the front standoff 86. This shape controls the entry point and the height of the suture. This facilitates the alignment of the suture wind therefore allowing for an easier removal of the suture.

This specific shape of the distal end 82 of the suture control arm 66 allows for the minimal opening and the faster closing of the opened channel and allows for speeds above 1000 rpm. In contrast to that, most pedal trays with conventional stylus known in the art run at 400 rpm or even less.

The suture control arm 66 is able to work with trays 14 known in the art both top loading trays and side loading trays. It works with trays with periphery shapes from round, oval, square and with side indentations (peanut shaped).

Figure 4:
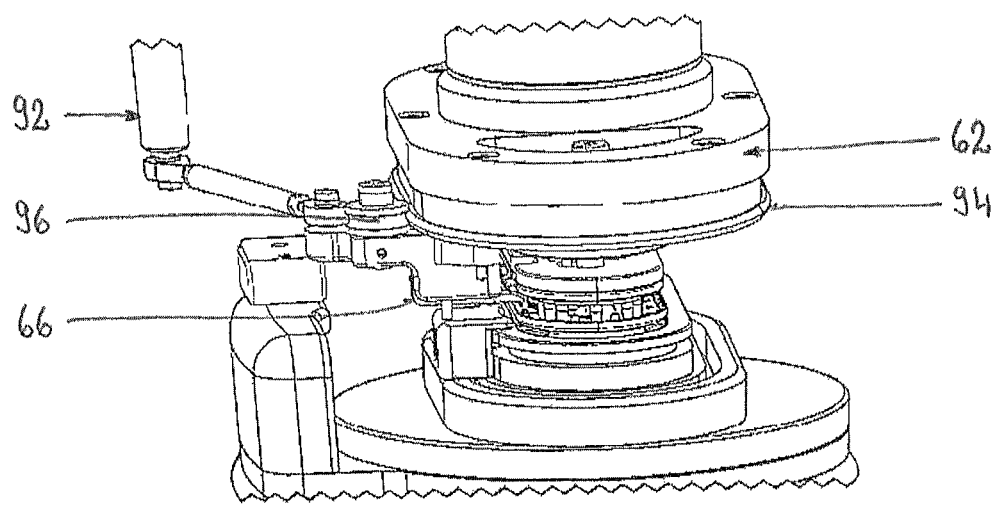
FIG. 4 is a schematic view of the winding station according to FIG. 1 or 2 with winding head, suture control arm and base member.
Figure 5:
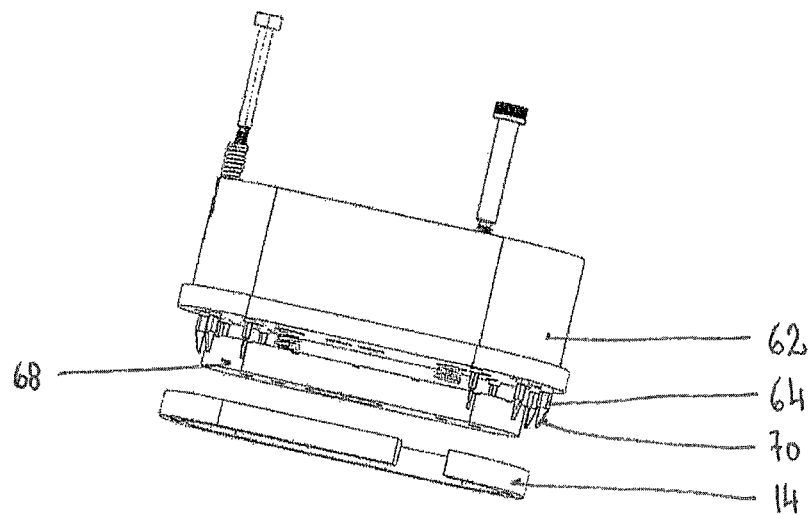
FIG. 5 is a schematic view of the winding head of the winding station according to FIG. 4.

The suture control arm 66 is mounted to a base member 92 (see FIG. 4). The winding head 62 of the winding station 60 has an outer ring 94. This outer ring 94 maintains the relative relationship between the winding station 60 and the base member 92. For this purpose the base member 92 has a running pulley 96 piloted by the outer ring 94. During the winding process, the winding head 62 is rotated. The base member 92 is not rotated but it can adapt to the relative position of the winding head 62.

This winding station 60 can wind trays with vacuum present or without vacuum present. If there is no vacuum present during the winding, it is usually necessary to have the lid placed directly after the needle parking and before starting the winding of the suture. Therefore, in this case the fifth station 100 should be placed after the third station 46 and before the fourth station 60.

The fifth station 100 is a printing and lid placement station. In this station, the lids of the trays 14 are loaded from a stack onto a line 102. In contrast to that, there could also be fan-fold lids, which are separated at the end of the line 102. The lids could be pre-printed paper lids of plastic lids or the like. This type of station 100 is widely used in the art so it is not described in detail.

The sixth station 104 is the lid attachment station. The lid could be attached by using ultrasonic sound or heated die, for example. By using ultrasonic sound or heated die it is possible to deform the standoff members of the trays, thereby locking the lid in place. This type of station 104 is widely used in the art so it is not described in detail.

The seventh station 106 is an offloading station. After offloading, the trays 14 are usually transported to an intermediate inspection station (not shown). This type of station 106 is widely used in the art so it is not described in detail. The intermediate inspection station is usually the station where all camera inspections are performed. The tray 14 is then transferred to an outfeed section 108 which can be a belt or a magazine, for example. It could also be transferred to a reject area. This kind of intermediate inspection station is widely used in the art so it is not described in detail.

The eighth station 110 is an open station for further options. For example, this station 110 could be used for a camera check in order to confirm the offloading of the tray.

The manual suture winding machine 10 is loaded and unloaded manually. In contrast to that, the semi-automatic suture winding machine 12 as shown in FIG. 2 is loaded and unloaded automatically.

In contrast to the circular layout of the rotary dial 22, there could also be an inline form for the suture winding machine 10 or 12. It is also possible to have a combination of a rotary dial 22 and an inline form.

What is claimed is:

1. A machine for winding suture into a suture tray package comprising:
    a base platform
    a plurality of package nests, each package nest comprising at least two locating pins extending up from the package nests,
    a first workstation for placing an empty tray onto one of the package nests,
    a further workstation for feeding a needle with an attached suture in the tray and parking said needle in the tray,
    a winding station for winding the suture into a winding channel of the tray, said winding station comprising
        a rotatable winding head with a plurality of configurable suture guiding pins, the guiding pins being configured as to engage a floor of the tray and to keep it flat,
        a suture control arm, said suture control arm having a proximal end, a distal end, a top side and a bottom side, said distal end of the suture control arm having a front standoff and a rear standoff incorporating a suture guiding channel,
        a base member for mounting the suture control arm to the base platform,
    an offloading station for removing said trays from the package nests,
    wherein
    the winding station further comprises a stripper plate for pushing the wound suture off the suture guiding pins,
    there is a lid placement station positioned at the base platform and configured to place a lid onto one of the package nests,
    there is a lid attachment station positioned at the base platform separate from the lid placement station and configured to attach the lid to the tray while the tray is in one of the package nests.

2. The machine according to claim 1, wherein the stripper plate is attached to the rotatable winding head.

* * * * *